Figure 1:
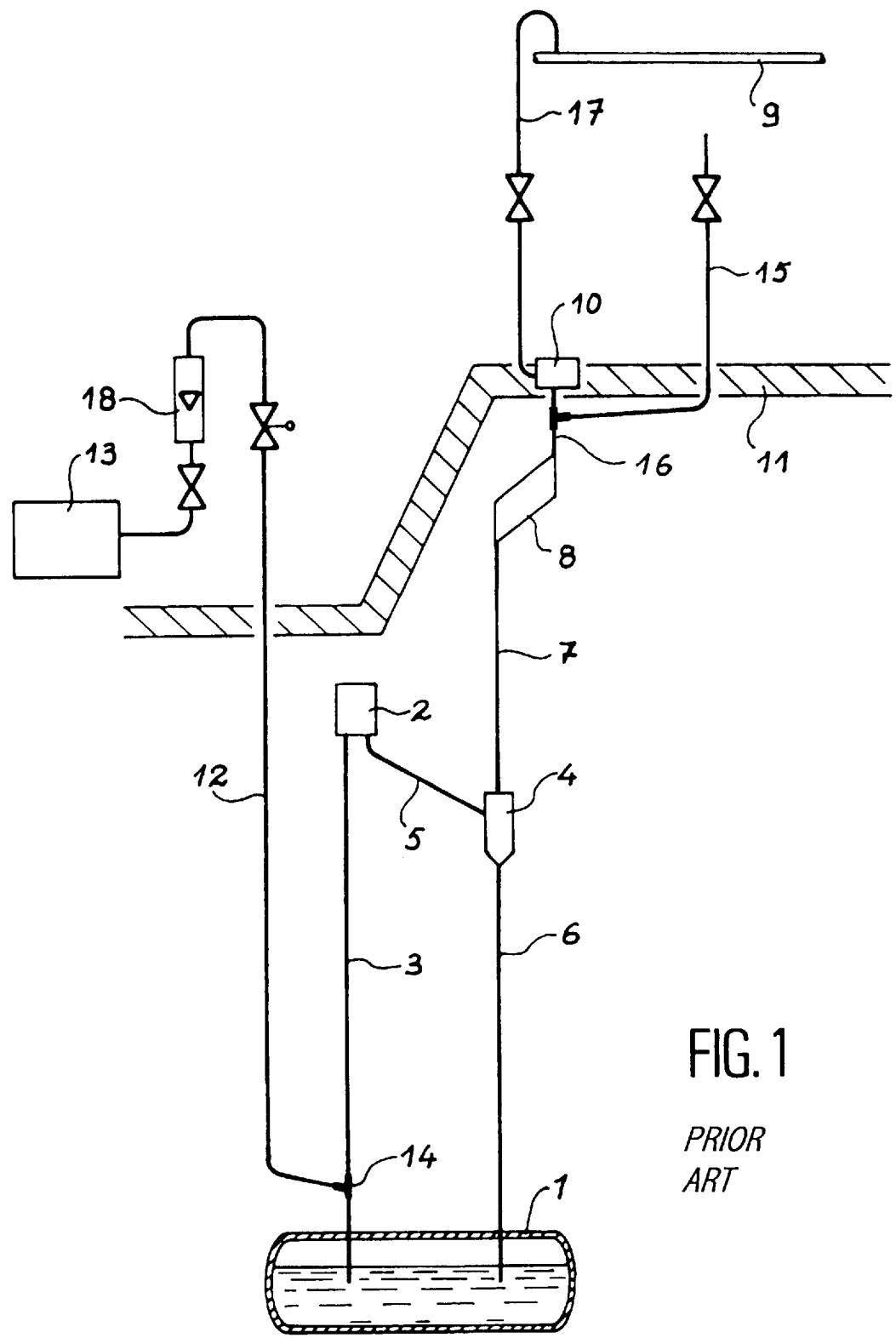

United States Patent
Allain et al.

[11] Patent Number: 5,817,953
[45] Date of Patent: Oct. 6, 1998

[54] METHOD AND APPARATUS FOR RINSING A DEVICE FOR CIRCULATING A LIQUID FOR SAMPLING PURPOSES

[75] Inventors: Jean-Guy Allain; Jean-Louis Kermorgant, both of Equeurdreville; Michel DuPont, Martinvast, all of France

[73] Assignee: Compagnie Generale Des Matieres Nucleaires, Velizy-Villacoublay, France

[21] Appl. No.: 922,428

[22] Filed: Sep. 3, 1997

Related U.S. Application Data

[63] Continuation of Ser. No. 500,966, filed as PCT/FR94/01372 Nov. 24, 1994, abandoned.

[30] Foreign Application Priority Data

Nov. 26, 1993 [FR] France ................................. 93 14184

[51] Int. Cl.⁶ .................................................. G01N 1/14
[52] U.S. Cl. ...................................... 73/863.83; 73/864.34
[58] Field of Search .......................... 73/863.83, 864.34, 73/864.35, 864.31

[56] References Cited

U.S. PATENT DOCUMENTS 3,722,291  3/1973  Lindberg .
4,179,932  12/1979  Ranger .
5,220,947  6/1993  Cauquil et al. .

FOREIGN PATENT DOCUMENTS 0079283  5/1983  European Pat. Off. .
0296917  12/1988  European Pat. Off. .
0472457  2/1992  European Pat. Off. .
2229422  9/1990  United Kingdom .
88/03065  5/1988  WIPO .

OTHER PUBLICATIONS

Database WPI, Section CH, Week 7413, Derwent Publications Ltd., London, GB; Class J04, AN 74–24344V C13 & SU,A,388 212 (Mineral Products Mech.) 31 Oct. 1973.

*Primary Examiner*—Robert Raevis
*Attorney, Agent, or Firm*—Pearne, Gordon, McCoy & Granger LLP

[57] ABSTRACT

The invention relates to a process for rinsing a device for circulating a liquid between a storage tank (1) and a sampling head (2) from a supply pipe (3) to which is connected a motor air pipe (12). The rinsing or washing consists of injecting a rinsing or washing fluid into the supply pipe (3) or into the motor air pipe (12), the latter being supplied with gas during the rinsing or washing of the device.

23 Claims, 4 Drawing Sheets

METHOD AND APPARATUS FOR RINSING A DEVICE FOR CIRCULATING A LIQUID FOR SAMPLING PURPOSES

This is a continuation of application Ser. No. 08/500,966, filed Nov. 1, 1995, now abandoned.

The present invention relates to a process for rinsing a device for circulating a liquid for taking a sample. This type of device is more particularly used in the nuclear industry for taking radioactive liquid samples.

EP-A-296 917 discloses a device for the continuous circulation of a liquid for taking a sample or checking said liquid. The sampling circuit is placed under a vacuum, which causes the liquid in a tank to rise within a supply pipe. The injection of air makes it possible for the liquid to rise up to an intermediate container. The injected air is extracted by a pipe and, after degassing, the liquid reaches a sampling head. This sampling procedure is known as air-lift.

The presently used air-lift devices have the following characteristics. The pipes used for raising the sampled liquid have a small cross-section, the solutions to be analyzed contain precipitates, it is not possible to suddenly revent the installation at the end of activity due to the presence of a submerged separator. In addition, there is a generalization of the tank or cell bank systems with up to 24 sampling possibilities, which leads to samples sometimes being taken from cells or tanks which are often remote from the bank. This leads to the use of small gradient pipe sections, which helps to give rise to sedimentation risks.

In the case of a clogging of the air-lift pipes, certain installations make it possible to subject the plug or stopper to a chemical action. It is also possible to act in a preventative manner by carrying out, at the end of activity, a systematic washing or rinsing of all the pipes of feeding in large quantities of water at a high flow rate (80 to 800 l/h under a pressure of approximately 7 bars). Before starting off operation, it is also possible to carry out a flow test, which involves the consumption of the sampling jugs containing highly active waste.

Other, more recent installations do not offer the possibility of a systematic rinsing of the all the air-lift pipes due to the enormous quantities of water needed for such an operation. However it is vital, particularly with the generalization of cell bank systems, to offer a possibility of the effective rinsing or washing of pipes which are liable to clog. This rinsing must also be performable at low cost.

The invention provides a solution to these problems. It consists of connecting a pipe carrying a rinsing fluid to one of the pipes positioned upstream of a sampling head and preferably to the air-lift motor air pipe, in order to admit a preregulated fluid flow rate. The rinsing fluid injection takes place whilst supplying the motor air pipe with gas.

The invention therefore relates to a process for rinsing a device for circulating a liquid between a storage tank and a sampling head located at a higher level than that of the free surface of the liquid contained in the tank and comprising:

a supply pipe for transporting the liquid between the storage tank and the sampling head, a compressed gas source connected by a so-called motor air pipe to the supply pipe in a so-called air-lift T zone, a separator located at an intermediate level between the sampling head and the free surface of the liquid contained in the storage tank and having an upper part and a lower part, a pipe connecting the sampling head to the separator, a pipe, called a splash head, connecting the upper part of the separator to means making it possible to produce a vacuum, a return pipe connecting the lower part of the separator to the storage tank, characterized in that it consists of injecting a rinsing fluid into the supply pipe or into the motor air pipe, the latter being supplied with gas during the rinsing of the device.

If the rinsing fluid is injected below the air-lift T into the supply pipe, its flow rate is preferably between 1 and 1.8 times the nominal flow rate of the device.

If the rinsing fluid cannot be injected into the supply pipe and if the motor air pipe is equipped with a rotameter and has no diaphragm, the rinsing fluid is injected in the vicinity of the rotameter.

If the motor air pipe is supplied with a diaphragm, the rinsing fluid is injected between the diaphragm and the air-lift T. The rinsing fluid can be injected just below the diaphragm in order to permit an isolated rinsing of said diaphragm.

If the device is provided with a stabilizer connected below the air-lift T, the rinsing fluid is injected via said stabilizer.

The rinsing fluid can be firstly injected during a predetermined time during which there is a progressive decrease of the flow rate of the gas supplying the motor air pipe for rinsing that part of the supply pipe positioned below the air-lift T by detachment of the liquid flow rate in the supply pipe.

Rinsing can be performed automatically at the end of a sequence of circulating storage tank liquid by the device.

Advantageously, the gas supplying the motor air pipe during the rinsing of the device is supplied by the compressed gas source.

The invention is described in greater detail hereinafter relative to non-limitative embodiments and with reference to the attached drawings, wherein show:

FIG. 1 Diagrammatically and according to the prior art, a device for circulating a liquid with a view to taking a sample.

Figure 2:
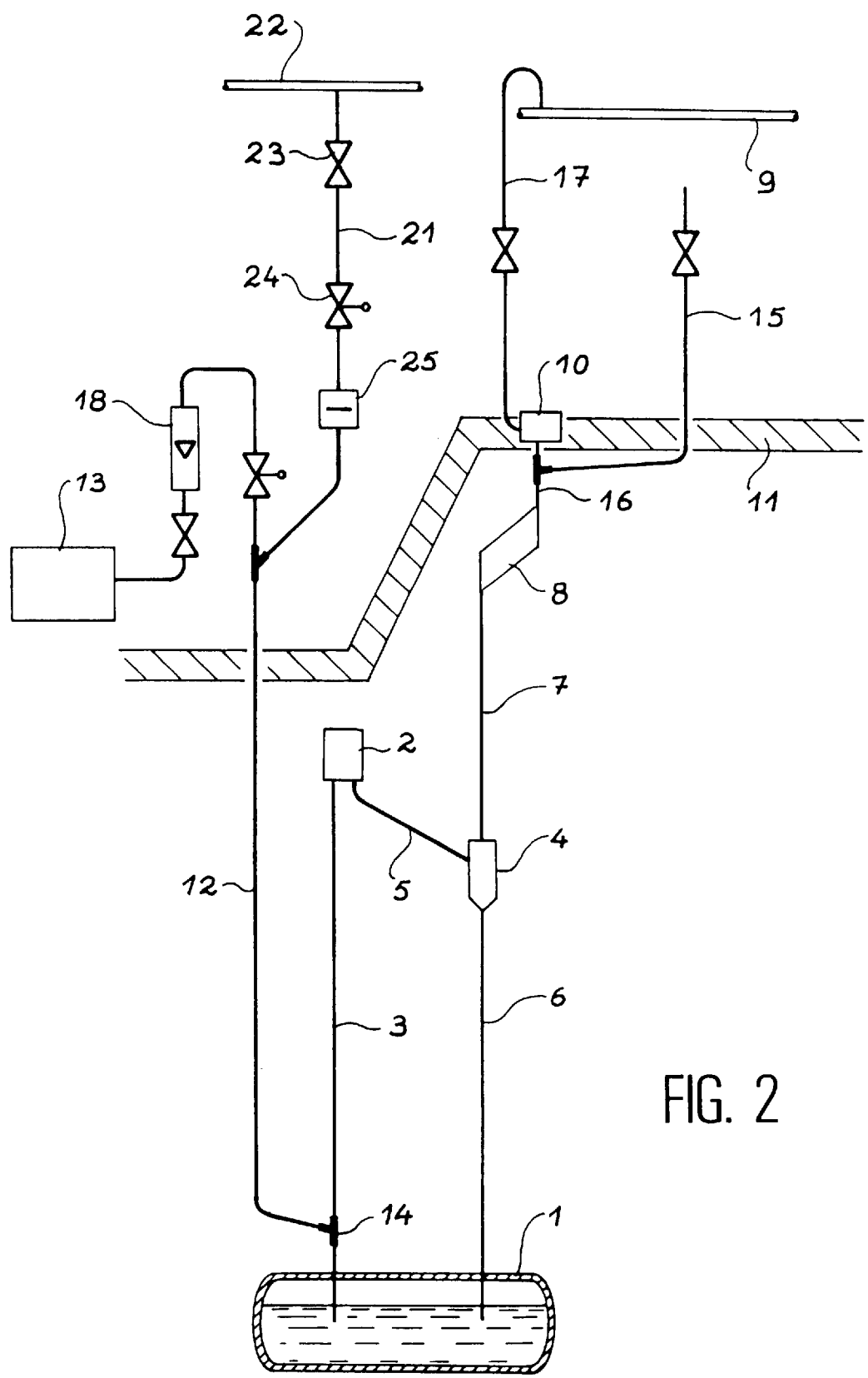

FIG. 2 The application of the process according to the invention to the prior art device shown in FIG. 1.

Figure 3:
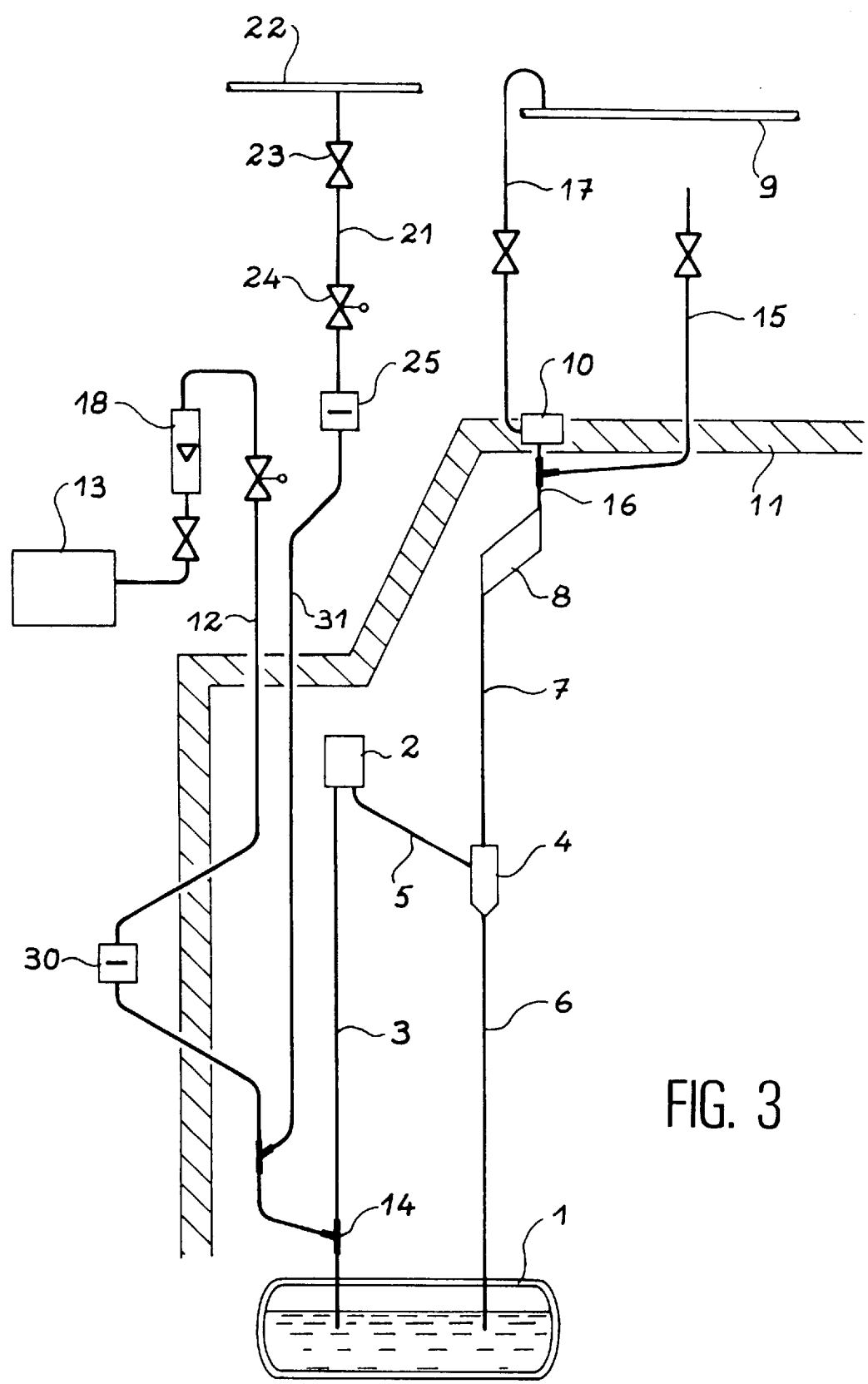

FIG. 3 Another application of the process according to the invention to said prior art device.

Figure 4:
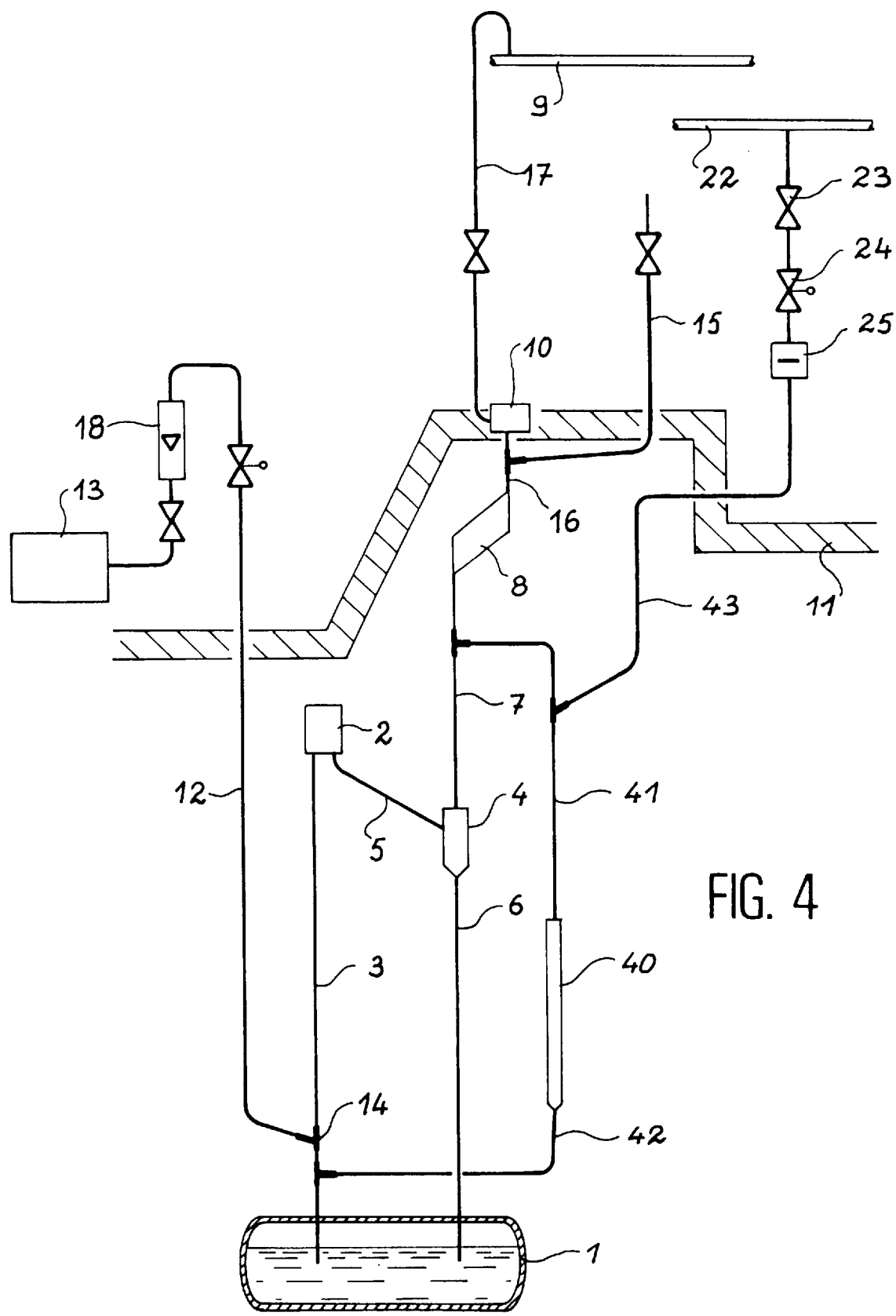

FIG. 4 Another application of the process according to the invention to said prior art device.

FIG. 1 illustrates a known device for the continuous circulation of a liquid contained in a storage tank 1. The circulation is intended to bring a certain liquid quantity up to the sampling head 2, the unsampled liquid being returned to the tank 1. The sampling head 2 is connected to the tank 1 by a supply pipe 3 immersed in the tank liquid. The gradient of the pipe 3 must be equal to or greater than 35%. The sampling head 2 is located above the tank 1 and at a level higher than that of the free surface of the liquid contained in the tank 1.

The device also incorporates a separator 4 positioned between the sampling head 2 and the storage tank 1. The upper part of the separator 4 is linked with the sampling head 2 by a pipe 5, whose gradient is equal to or greater than 5%. A return pipe 6, having a gradient equal to or greater than 5%, links the lower part of the separator 4 and the storage tank 1. The liquid not sampled by the head 2 consequently returns to the tank 1 by the circuit comprising the pipe 5, the separator 4 and the pipe 6.

A pipe 7 equipped with a splash head 8 links the upper part of the separator 4 with an apparatus making it possible to create a vacuum, e.g. a vacuum pump. The link between the splash head 8 and the vacuum pipe 9 connected to the vacuum pump comprises a filter 10 located in the protective wall 11 surmounting the storage tank 1 and the device for circulating the liquid from the tank 1. The pipes 16 and 17 provide the connections between the splash head, filter and vacuum pipe.

A so-called motor air pipe 12 links a compressed gas source 13 and the supply pipe 3 passing through the wall 11. The pipe 12 is equipped with a rotameter 18. The junction of the pipes 12 and 3 is in the vicinity of the storage tank 1 in a so-called air-lift T zone 14. The part of the supply pipe 3 located below the T 14, called the air-lift base, has a gradient equal to or greater than 2%.

The device operates in the following way. When the apparatus permitting the creation of a vacuum in the pipe 9 is started up, a vacuum is produced in the device and in particular in the supply pipe 3. The liquid contained in the storage tank 1 rises in said pipe. The compressed gas source (e.g. an air source) 13 is started up so as to blow gas into the supply pipe 3 and into the mass of liquid contained therein. As the apparatus making it possible to produce a vacuum is still operating, bubbles are formed in the pipe 3 and said bubbles rise and entrain the liquid towards the head 2. After passing into the head 2, where part of the liquid is sampled, the liquid returns to the storage tank 1. Thus, a mixture of gas and liquid enters the separator 4. As the latter is connected to the vacuum-producing apparatus by the pipe 7, the gas is extracted by the latter, whereas the liquid collects in the lower part of the separator and drops by gravity into the storage tank following the pipe 6. The splash head 8 permits the separation of liquid droplets which could be entrained with the gas along the pipe 7.

The rinsing with the prior art device takes place by injecting water by pipe 15, which traverses the wall 11 and is connected to the pipe 16 linking the splash head 8 with the filter 10. Thus, it is possible to rinse or wash the splash head 8, the separator 4 and the pipes 6 and 7.

FIGS. 2 to 4 illustrate the performance of the process according to the invention, the same references as in FIG. 1 designating the same elements. A description will now be given of several rinsing and washing possibilities according to the invention, i.e. with the air-lift in operation.

Rinsing performed by branching a water pipe to the supply pipe 3, above the air-lift T 14 (in order to optionally place it above the dome of the tank 1 in the case of a submerged T) leads to a relatively significant dilution of the active solution contained in the tank. A complete rinsing of the device is only obtained for a very pronounced rinsing flow rate/air-lift liquid flow rate ratio. As a result of a bending or damping effect, it is also possible for the rinsing liquid to flow directly to the tank 1 without rinsing the complete device.

Rinsing performed by branching a water pipe below the air-lift T 14 gives very satisfactory results when the rinsing flow rate is between 1 and 1.8 times the air-lift liquid flow rate. Under these conditions, the device is entirely rinsed. With a submerged air-lift T, the problem arises of perforating the dome of the tank 1 if there is no pipe waiting.

Rinsing performed by branching a water pipe to the motor air pipe is satisfactory. The tests performed reveal two interesting possibilities illustrated by FIGS. 2 and 3.

According to FIG. 2, a water pipe 21 is branched to the motor air pipe 12 above the wall 11, in the vicinity of the rotameter 18 if there is no diaphragm on the pipe 12. The air-lift T may or may not be submerged. The rinsing flow rate is advantageously set between 0.8 and 1.5 times the normal air-lift flow rate. The water pipe 21 is connected to a line 22 of the silica-extracted water circuit. It has a manual valve 23, an electrovalve 24 and a diaphragm 25. With such an arrangement, it is possible to entirely rinse the device from the air-lift base to the sampling head 2, as well as the base of the separator 4 and the return circuit to the tank. As this rinsing takes place with air-lift in operation it can easily be automated at the end of the air-lift circulation sequence.

Three minutes is more than adequate for correct rinsing. In practice, rinsing rates are between 50 and 120 l/h, which leads to the arrival of 1.5 to 6.4 liters of solution in the storage tank. Generally, it is possible to ignore the dilution taking place during rinsing.

FIG. 3 illustrates the case where, in order to improve the operation of the air-lift, a diaphragm 30 has been installed on the motor air pipe 12. The branching of the rinsing water pipe 31 is then performed between the diaphragm 30 and the air-lift T 14. The rinsing flow rate is advantageously set between 0.6 and 1.6 times the normal air-lift flow rate. If it is also wished to rinse the diaphragm 30, it is merely necessary to branch the pipe 31 in the vicinity of the diaphragm (e.g. 10 or 15 cm below). It is possible to start a rinsing sequence in isolated form for said diaphragm.

FIG. 4 illustrates the case where the device incorporates a stabilizer or calming device 40 making it possible to improve its stability. The stabilizer is connected on the one hand to the pipe 7 by a pipe 41 and on the other to the supply pipe 3 beneath the air-lift T 14 by a pipe 42. In this case, the rinsing water pipe 43 is connected to the pipe 41.

The tests which have taken place have proved very satisfactory. The rinsing process according to the invention is effective and relatively easy to perform. It is no longer necessary to intervene on the different components of the device.

We claim:

1. Process for rinsing a device for circulating a liquid between a storage tank and a sampling head located at a higher level than that of the free surface of the liquid contained in the tank, the device comprising:

a supply pipe for transporting the liquid between the storage tank and the sampling head, a compressed gas source connected by a motor air pipe to the supply pipe in an air-lift T zone, a separator located at an intermediate level between the sampling head and the free surface of the liquid contained in the storage tank and having an upper part and a lower part, a pipe connecting the sampling head to the separator, a pipe connecting the upper part of the separator to means making it possible to produce a vacuum, a return pipe connecting the lower part of the separator to the storage tank, the process comprising injecting a rinsing fluid into one of the supply pipe and the motor air pipe, the motor air pipe being supplied with gas during the rinsing of the device.

2. Process according to claim 1, wherein as the rinsing fluid is injected into the supply pipe below the air-lift T zone, it is injected with a flow rate between 1 and 1.8 times the nominal flow rate of the device.

3. Process according to claim 2, wherein as the device is provided with a stabilizer connected below the air-lift T, the rinsing fluid is injected via the stabilizer.

4. Process according to claim 1, wherein the rinsing fluid is injected into the motor air pipe.

5. Process according to claim 4, wherein as the motor air pipe is equipped with a rotameter and has no diaphragm, the rinsing fluid is injected in the vicinity of the rotameter.

6. Process according to claim 5, wherein the rinsing fluid is injected at a flow rate between 0.8 and 1.5 times the nominal flow rate of the device.

7. Process according to claim 6, wherein as the motor air pipe is provided with a diaphragm, the rinsing fluid is injected between the diaphragm and the air-lift T.

8. Process according to claim 7, wherein the rinsing fluid is injected at a flow rate between 0.6 and 1.6 times the nominal flow rate of the device.

9. Process according to either of the claims 7 or 8, wherein the rinsing fluid is injected just below the diaphragm to permit an isolated rinsing of the diaphragm.

10. Process according to claim 1, wherein the rinsing fluid is firstly injected for a given period of time, followed by a progressive reduction of the flow rate of the gas supplying the motor air pipe in order to rinse that part of the supply pipe located below the air-lift T by detachment of the liquid flow rate in the supply pipe.

11. Process according to claim 1, wherein the rinsing takes place automatically at the end of a sequence of circulating the liquid of the storage tank by the device.

12. Process according to claim 1, wherein the rinsing fluid is silica-extracted water.

13. Process according to claim 1, wherein the gas supplying the motor air pipe during the rinsing of the device is supplied by the compressed gas source.

14. A process for rinsing a device for circulating a liquid between a storage tank and a sampling head, said device including:
   a supply pipe connecting the storage tank to the sampling head;
   a motor air pipe connected to the supply pipe at an air-lift T zone;
   a compressed gas source connected to the motor air pipe;
   a separator for connection to a vacuum source;
   a pipe connecting the separator to the sampling head; and
   a return pipe connecting the separator to the storage tank;
   said process comprising the steps of:
      injecting a rinsing fluid into one of the supply pipe and the motor air pipe; and
      supplying the motor air pipe with gas from the compressed gas source at the same time the rinsing fluid is injected into said one of the supply pipe and the motor air pipe.

15. The process of claim 14 wherein the rinsing fluid is injected into the motor air pipe.

16. The process of claim 15 wherein the rinsing fluid is injected at a flow rate between 0.8 and 1.5 times the flow rate of the liquid when the liquid is circulated between the storage tank and the sampling head.

17. The process of claim 14 wherein the rinsing fluid is injected into the supply pipe.

18. The process of claim 17 wherein the rinsing fluid is injected at a flow rate between 1 and 1.8 times the flow rate of the liquid when the liquid is circulated between the storage tank and the sampling head.

19. A device for circulating a liquid between a storage tank and a sampling head, said device comprising:
   a supply pipe connecting the storage tank to the sampling head;
   a motor air pipe connected to the supply pipe at an air-lift T zone;
   a separator for connection to a vacuum source;
   a pipe connecting the sampling head to the separator;
   a return pipe connecting the separator to the storage tank;
   a rinse pipe connecting one of the supply pipe and the motor air pipe to a source of rinse fluid; and
   a compressed gas source connected to the motor air pipe, said compressed gas source being operable to supply gas to the motor air pipe while rinse fluid is being supplied to said one of the supply pipe and the motor air pipe, said gas helping move the rinse fluid through the supply pipe, thereby rinsing the supply pipe.

20. The device of claim 19 wherein the rinse pipe is connected to the supply pipe.

21. The device of claim 20 wherein the rinse pipe is connected to the supply pipe below the air-lift T zone.

22. The device of claim 19 wherein the rinse pipe is connected to the motor air pipe.

23. The device of claim 22 further comprising a diaphragm connected into the motor air pipe; and
   wherein the rinse pipe is connected to the motor air pipe between the diaphragm and the air-lift T zone.

\* \* \* \* \*